United States Patent [19]
Arnett et al.

[11] Patent Number: 6,135,995
[45] Date of Patent: Oct. 24, 2000

[54] ELECTRONICALLY PULSED LASER SYSTEM

[75] Inventors: Michael Arnett, Menlo Park, by Dorothy Arnett, guardian; Robert J. Rorden, Los Altos Hills; Gregory Dumond, Santa Clara; Jerzy Orkiszewski, Livermore; David Dewey, Sunnyvale; David Trost, San Francisco, all of Calif.

[73] Assignee: Coherent, Inc., Santa Clara, Calif.

[21] Appl. No.: 08/710,577

[22] Filed: Sep. 19, 1996

Related U.S. Application Data

[60] Provisional application No. 60/004,345, Sep. 26, 1995.

[51] Int. Cl.[7] .................................................... A61N 5/06
[52] U.S. Cl. .............................................................. 606/12
[58] Field of Search ................................. 606/2, 3, 10–13

[56] References Cited

U.S. PATENT DOCUMENTS

| | | |
|---|---|---|
| 3,766,492 | 10/1973 | Rosati . |
| 4,316,467 | 2/1982 | Mucherheide . |
| 4,388,924 | 6/1983 | Weissman et al. . |
| 4,470,414 | 9/1984 | Imagawa et al. . |
| 4,564,012 | 1/1986 | Shimada et al. . |
| 4,573,465 | 3/1986 | Sugiyama et al. . |
| 4,580,557 | 4/1986 | Hertzmann . |
| 4,601,037 | 7/1986 | McDonald . |
| 4,641,649 | 2/1987 | Walinsky et al. . |
| 4,657,013 | 4/1987 | Hoerenz et al. . |
| 4,785,456 | 11/1988 | Kaplan . |
| 4,950,268 | 8/1990 | Rink . |
| 5,390,204 | 2/1995 | Yessik et al. ............................. 606/12 |
| 5,498,935 | 3/1996 | McMahan et al. ....................... 606/12 |

FOREIGN PATENT DOCUMENTS 2493559   5/1982   France ........................ G05D 25/00

*Primary Examiner*—David M. Shay
*Attorney, Agent, or Firm*—Limbach & Limbach L.L.P.

[57] ABSTRACT

Typically, a laser emits significant energy after a control signal is generated to disable the power supply. The inherent delay between generation of a control signal for shutting off a laser power supply and actual termination of an output beam pulse in response to the control signal, is compensated in the context that the control signal is generated automatically upon coincidence of measured output beam power with a preset threshold value. Power supplied to a laser is modulated to cause generation of a pulsed laser output beam. The cumulative energy of each output beam pulse is monitored and a feedback signal indicative of measured output beam pulse energy is supplied to the power supply. The feedback signal is compared with a user-selected threshold value, and a control signal is generated for terminating the output beam pulse (by terminating input power to the laser) when the measured output pulse energy reaches the threshold value. By generating the threshold signal to have a value representing a threshold output beam pulse energy that is lower than a desired output beam pulse energy, the threshold signal is generated in a manner which compensates for the inherent delay between generation of the control signal and the actual termination of the output beam pulse in response to the control signal. This prevents delivery of significant output beam energy in excess of a user-selected amount.

17 Claims, 9 Drawing Sheets

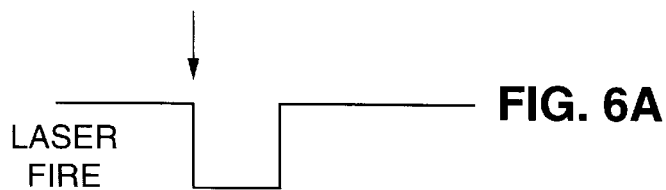
FIG. 6A
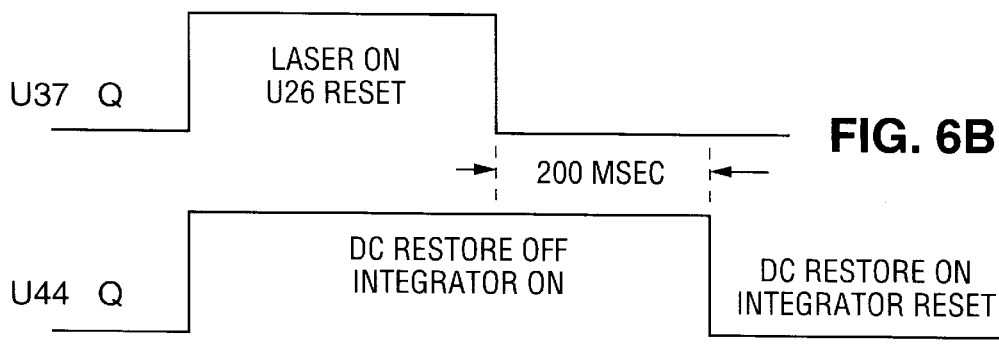
FIG. 6B
FIG. 6C
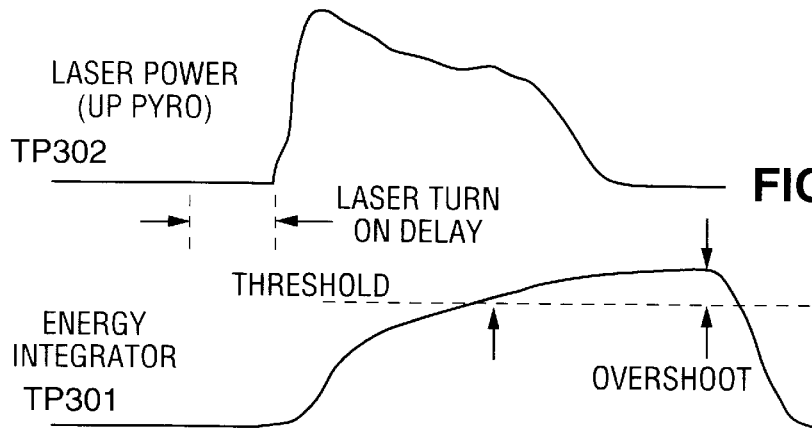
FIG. 6D
FIG. 6E
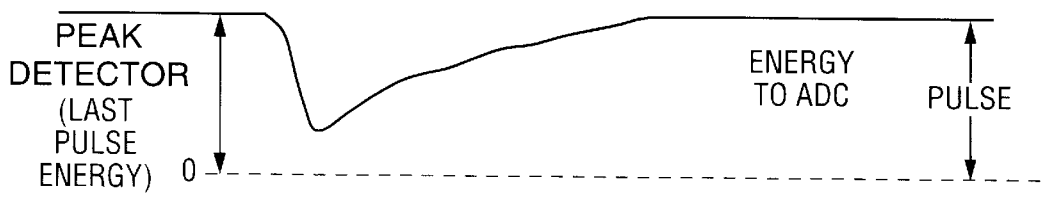
FIG. 6F
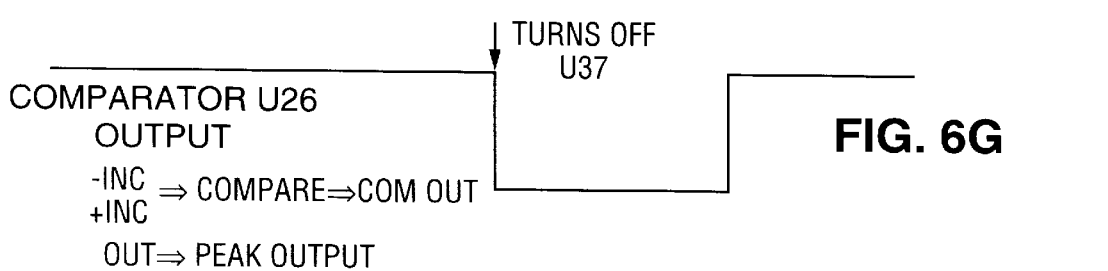
FIG. 6G

ELECTRONICALLY PULSED LASER SYSTEM

RELATED APPLICATIONS

This application claims priority under 35 U.S.C. § 120 of Provisional Patent Application Number 60/004,345, filed on Sep. 26, 1995.

FIELD OF THE INVENTION

The invention relates to electronically pulsed laser systems. In a preferred embodiment, the invention is an electronically pulsed laser system suitable for use for surgery or other medical applications.

BACKGROUND OF THE INVENTION

Gas (e.g., $CO_2$) lasers for medical use have been manufactured with a control system which adjusts laser operation parameters during an initial test operation with the output beam blocked. A totally reflective mirror is directed to a thermal average power sensor. The output of the power sensor is digitized and provided to a control processor. Pulse repetition rate is derived by the processor from control panel selections, by a user (e.g., a doctor) of power and energy. Pulse width is determined by the processor to achieve the desired pulse energy. These initially determined laser operation parameters are used during treatment without change. However, gas (and, in particular, $CO_2$) lasers vary output by approximately plus or minus 10% over time and temperature ranges, for a constant input.

One attempt to solve this problem is described in U.S. Pat. No. 4,950,268, issued Aug. 21, 1990. With reference to FIG. 4 of U.S. Pat. No. 4,950,268, a laser system operating in a pulsed-mode employs measured output beam pulse energy as a feedback signal in a laser power control circuit. When the measured energy of an output beam pulse exceeds a preset value, op amp 42 (of FIG. 4 of U.S. Pat. No. 4,950,268) emits a control signal to reset AND gate 32. In response to the control signal, the laser power supply is "squelched." However, the system of U.S. Pat. No. 4,950,268 is subject to the following serious disadvantage: the laser may (undesirably) emit significant energy after op amp 42 emits a control signal to squelch the power supply, because of stored energy in the lasing medium and inherent time delays occurring during feedback signal generation and processing of the control signal.

SUMMARY OF THE INVENTION

The present invention solves the problem of the laser emitting significant energy after a control signal is generated to disable the power supply. In particular, the present invention compensates for the inherent delay between generation of a control signal for shutting off a laser power supply and actual termination of an output beam pulse in response to the control signal, in the context that the control signal is generated automatically upon coincidence of measured output beam power with a preset threshold value.

The system of the invention includes a laser and a power supply for supplying pulses of DC or periodically varying (AC) power to the laser. The system includes circuitry that modulates the power supplied to the laser to cause generation of a pulsed laser output beam.

The system also includes circuitry that monitors the cumulative energy (rather than power) of each output beam pulse and supplies a feedback signal indicative of measured output beam pulse energy to the power supply. The system compares the feedback signal with a user-selected threshold value, and generates a control signal for terminating the output beam pulse (by terminating input power to the laser) when the measured output pulse energy reaches the threshold value.

Significantly, by generating the threshold signal to have a value representing a threshold output beam pulse energy that is lower than a desired output beam pulse energy, the system generates the threshold signal in a manner which compensates for the inherent delay between generation of the control signal and the actual termination of the output beam pulse in response to the control signal. This prevents delivery of significant output beam energy in excess of a user-selected amount. The delay compensation can be implemented by setting the threshold value, T, to be equal to T=E−O, where E is the user-selected output beam pulse energy and O is an estimate of the pulse energy that will be delivered during the delay period required to perform the following operations: generate a pulse termination control signal in response to the energy measurement, supply the pulse termination control signal to the laser power supply and, in response to the control signal, discharge energy which is stored in the electrical system and the laser medium. In some embodiments, the system selects a different threshold value (T=E−O) from a prestored look-up table for each user-selected value E, by reading the look-up table value (T) indexed by the user-selected value E.

In other embodiments, the system iteratively improves its estimate of the offset value O over several pulse generation cycles (all for the same user-selected value E) in the following manner. For each output beam pulse, the system measures the total output beam pulse energy (from beginning through termination), computes the difference between the measured total energy and the user-selected value E. The system uses the computed difference as a feedback signal to improve its estimate of the offset value O (and thus improve its estimate of threshold value T=E−O) for terminating the next pulse.

In embodiments in which the laser is a gas laser (such as a $CO_2$ laser), the system does not control instantaneous power (amplitude) of the output beam pulse, but monitors output pulse energy and controls the duration of each output beam pulse, thereby controlling the delivered energy of each output beam pulse.

The output beam pulse energy can be monitored by monitoring the output beam's instantaneous power using a detector. Alternately, the output beam pulse energy can be determined by monitoring the beam's instantaneous amplitude using a detector and continually processing the detector output to compute an instantaneous power signal from the measured instantaneous amplitude. A signal indicative of the instantaneous power of the output beam (of the current output beam pulse, if the beam is a pulsed beam) is integrated to generate a signal indicative of cumulative output beam energy (cumulative energy in the current output beam pulse, if the beam is a pulsed beam).

The invention is particularly suitable for use in surgical applications, but is also useful for other applications.

BRIEF DESCRIPTION OF THE DRAWINGS

FIGS. 6A through 6G is a timing diagram of the significant signals generated by the FIG. 5 circuit.

DETAILED DESCRIPTION OF THE PREFERRED EMBODIMENTS

Figure 1:
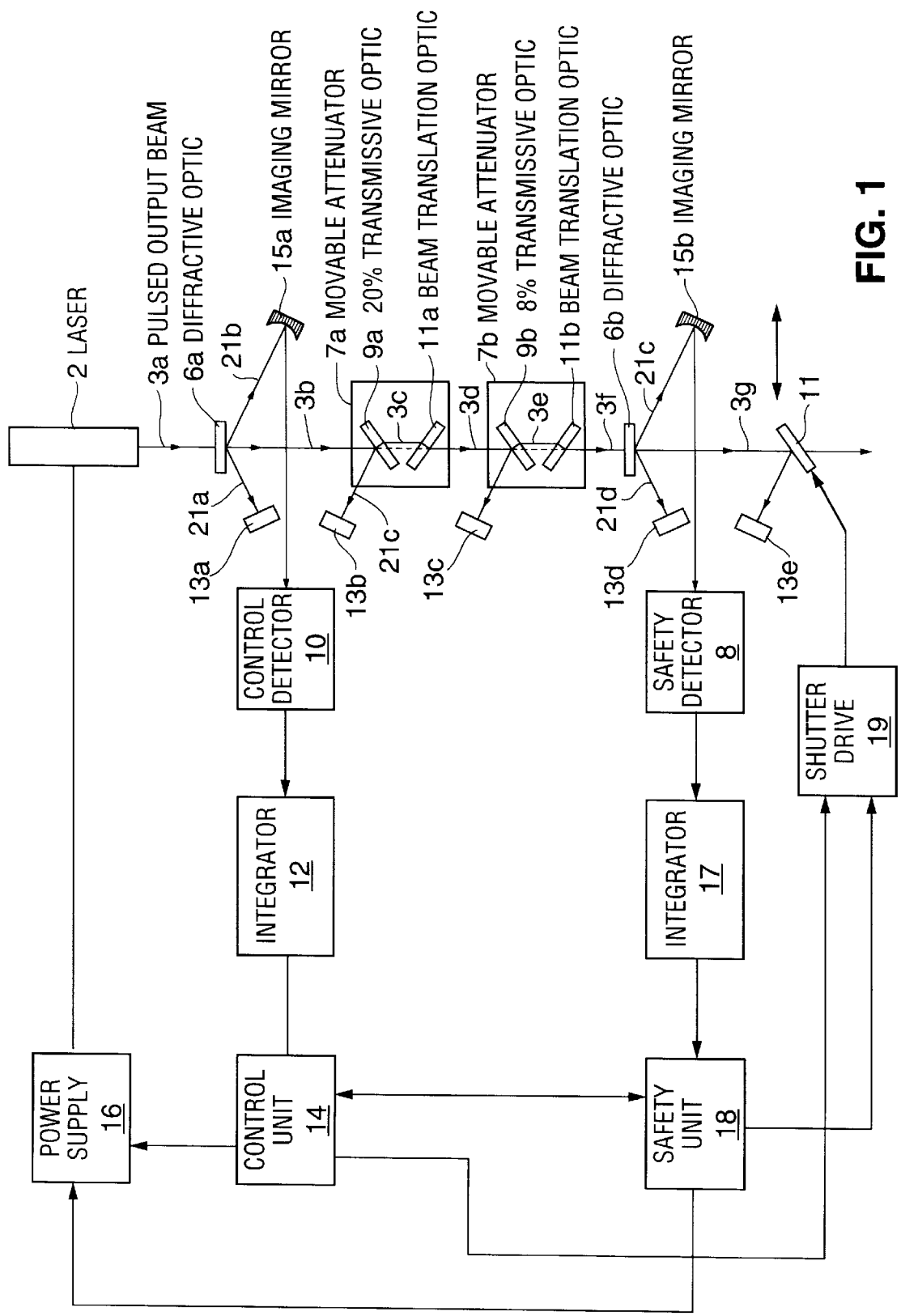
FIG. 1 is a block diagram of an embodiment of a system in accordance with the invention.

An embodiment of the system in accordance with the invention will be described with reference to FIG. 1. The FIG. 1 system includes laser 2 (which may be a gas laser such as a carbon dioxide laser) which emits a pulsed output beam 3a when appropriately powered. Laser 2 can alternatively be of the type not capable of continuous wave (CW) operation (such as a diode laser), or it can be a laser capable of CW operation.

Laser power supply 16 supplies electrical power to laser 2 in response to control signals from control circuit 14. In embodiments in which laser 2 is a radio frequency (RF) excited gas laser, power supply 16 supplies one or more pulses of RF power to excite a gas (or gas mixture) within laser 2 in response to each control signal, where each pulse of RF power has a duration sufficient to cause laser 2 to emit a pulse of duration.

Although one embodiment of power supply 16 supplies pulses or bursts of RF power to laser 2, other embodiments of the invention can employ another type of power supply (such as another AC power supply or a DC power supply) as power supply 16. Each embodiment of power supply 16 should be capable of modulating power (e.g., initiating and terminating a pulse of RF, AC or DC power) to laser 2 in response to control signals from control unit 14, to cause the laser to emit an output beam pulse 3a having duration matching a pre-selected parameter.

A diffractive beam sampling optical element 6a is mounted in the path of output beam 3a. This element is an anti-reflection coated disc of transparent material with a phase grating of pairs of parallel stripes. In each pair of stripes, one stripe is etched into the material, reducing the thickness of the material. Two symmetrical diffracted first order beams 21a and 21b are produced, each having a power approximately equal to 0.2% of the incident beam 3a. The remainder of the incident beam 3 is transmitted. The angle from the incident beam 3a to the diffracted beams 21a and 21b is determined by the width of the stripe pairs of the phase grating in the diffractive beam sampling element 6a. The power in the diffracted beams is determined by the depth of a single etched stripe in each pair. Diffracted beam 21a is absorbed by beam block 13a, while diffracted beam 21b is reflected by imaging mirror 15a to control detector 10. Control detector 10 thus receives a small (known) fraction of the energy in beam 3a. The remainder of beam 3a is transmitted through the diffractive optic 6a at zero degrees, as beam 3b.

The output signal from detector 10 is indicative of the instantaneous power of output laser beam 3a. The output signal from detector 10 is integrated by integration circuit 12 to generate a signal indicative of cumulative energy in the beam 3a (cumulative energy in the current output beam pulse, if beam 3a is a pulsed beam).

In some embodiments, detector 10 includes means for measuring beam 3a's instantaneous amplitude and means for continually processing a signal indicative of the measured instantaneous amplitude to generate an instantaneous power signal. The output signal from detector 10, which is indicative of instantaneous power of beam 3, is then integrated in integration circuit 12 to generate a signal indicative of cumulative energy in beam 3 (cumulative energy in the current output beam pulse, if beam 3 is a pulsed beam).

Two movable beam attenuators 7a and 7b are provided for optionally reducing the output beam power beyond the range of direct control of laser 2. Each attenuator 7a and 7b is movable by an electrically driven solenoid (not shown) into and out of the beam. Attenuator 7a includes a partially reflective coated transparent element 9a (e.g., 80% reflective and 20% transmissive). The partially reflective transparent element 9a reflects the reflected portion 21c of beam 3b to beam block 13b. The partially reflective transparent element 9a slightly displaces the transmitted portion 3c of beam 3b laterally. Beam translation optic 11a is provided to restore the beam 3c, as beam 3d, to what would otherwise have been the path of beam 3b were it not for the lateral displacement caused by element 9a.

Attenuator 7b is identical to attenuator 7a except that the partially reflective transparent element 9b transmits approximately 8% of the beam 3d (as beam 3e) and reflects approximately 92% of the beam (as beam 21d, to beam block 13c). Beam translation optic 11b is provided to restore the beam 3e, as beam 3f, to what would otherwise have been the path of beam 3d were it not for the lateral displacement caused by element 9b.

Beam 3f (which is the transmitted beam from diffractive beam sampling optical element 6a, whether or not attenuated by movable attenuators 7a and/or 7b) impinges onto diffractive optic 6b, which provides a small (known) portion of the beam energy in beam 3f (i.e., beam 21c), via imaging mirror 15b, to safety detector 8. (Another small portion of the beam energy in beam 3f (i.e., beam 21d) is absorbed by beam block 13c.) The output signal from safety detector 8 is integrated by integration circuit 17 to generate a signal indicative of cumulative energy in the beam 3f (cumulative energy in the current output beam pulse, if beam 3a is a pulsed beam).

A safety shutter 11 is provided to divert beam 21 to beam block 13e, under the control of shutter drive 19 (e.g., a solenoid). Shutter drive 19 is in turn controlled by safety unit 18 or control unit 14 responsive to the cumulative energy of beam 3a as indicated by the output signal from integrator 17 being above a desired value. That is, safety unit 18 includes circuitry that triggers insertion of shutter 11 in the path of beam 3g in response to the feedback signal from detector 8. In addition (or alternatively), safety unit 18 disables power supply 16 from driving laser 2 in response to the feedback signal from detector 8 indicative of an unsafe characteristic of beam 3a. In both cases, safety circuit 18 prevents delivery of beam energy to a patient upon occurrence of the unsafe condition.

Control unit 14 is preferably programmed to simulate the unsafe condition by sending an appropriate simulation signal to safety circuit 18, and to check for the proper system response to such simulation signal. Control unit 14 may be programmed to perform this checking operation periodically, at an appropriate rate (preferably before each use of the laser).

An embodiment of elements 10, 12, and 14 of FIG. 1 will next be described with reference to FIG. 2. In this embodiment, radiation detector 10 is implemented as pyroelectric detector 50. Detector 50 generates an output current that is directly related, in a known manner (as discussed in more detail below), to the power of the output beam portion incident thereon. Thus, the output current produced by pyroelectric detector 50 is indicative of the power of output beam 3. The output current signal from pyroelectric detector 50 is converted to a voltage, and amplified, by transimpedance amplifier 12A. The amplified voltage signal propagates over shielded cable 106 to a main control assembly.

In the main control assembly, the propagated amplified voltage from the pyroelectric detector 50 is provided to an integrator 12B, via a DC restorer 61. The DC restorer 61 may not be necessary when the detector 10 is not implemented as the pyroelectric detector 50. Whether or not the DC restorer 61 is provided, a signal that is indicative of the instantaneous power of output beam 3 (whether the output of the DC restorer 61 or the amplified voltage from the detector 50 directly), is integrated in integration circuit 12B. The integrated output signal asserted at the output of circuit 12B (sometimes referred to as a "beam energy signal") is indicative of the cumulative energy in output beam 3.

In response to a "laser fire" signal from a processor 66, a timer circuit 63 provides an "ON" signal to the laser power supply 16, via logic block 65. This causes laser power supply 16 to provide power to the laser 2. Also in response to the "laser fire" signal from processor 66, timer 63 releases a "reset" signal, RESET2, to enable the integration circuit 12B at appropriate times, for example to cause the beam energy signal output from circuit 12B to be indicative of the cumulative energy of only one pulse (as opposed to a sequence of two or more pulses) of output beam 3 in the case that beam 3 is a pulsed beam.

The beam energy signal asserted at the output of circuit 12B is also supplied to a first input of comparator circuit 72. The other input of comparator circuit 72 receives a threshold energy signal from digital-to-analog (D-to-A) converter 70. When the value of the beam energy signal has increased to a level which matches the value (T) of the threshold energy signal, comparator 72 provides a "clear" signal to timer 63. In response, timer 63 provides an "OFF" signal to laser power supply 16 (via logic block 65), which causes laser power supply 16 to cease providing power to laser 2. The threshold signal is generated by converting a digital threshold signal from microprocessor 66 to analog form in D-to-A converter 70, after microprocessor 66 has generated the digital threshold signal in a manner which compensates for inherent delay between generation of the control signal (by comparator 72) and the actual termination of a pulse of output beam 3 by laser 2 in response to the control signal. This prevents delivery of significant output beam energy in excess of a user-selected amount.

In a preferred embodiment, the delay compensation is implemented by setting the threshold value, T, to equal T=E−O, where "E" is a user-selected output beam pulse energy (input to processor 66 by a user operating computer input device, which is not shown) and "O" is an estimate of the output beam pulse energy that will be delivered during the delay period required to perform the following operations: generation of a pulse termination control signal in logic block 65 (in response to incidence of radiation on detector 50's electrode surface, processing of the resulting output of detector 50 in elements 51, 12A, and 12B, and assertion of a match signal at the output of comparator 72 indicating a match between the output signal from integrator 12B and the threshold signal from D-to-A converter 70), supply of the pulse termination control signal to laser power supply 16, and actual termination of the output beam pulse in response to reception of the pulse termination control signal at power supply 16. Actual termination of the output beam pulse in response to reception of the pulse termination control signal at power supply 16, due to stored energy in the lasing mechanism, accounts for the majority of the delay period.

The DC restorer 61 is now discussed. One type of pyroelectric detector is formed of a ceramic insulator, and charge is induced to move through the ceramic insulator when one surface of the insulator is heated by the output beam portion 3 incident thereon. The Model 420 M3 pyroelectric detector, manufactured by Eltec Instruments, Inc. of Daytona Beach, Fla. is of this type. The ceramic insulator pyroelectric detector 50 is essentially a capacitor. Initially, the charge flow to the capacitor is an accurate indication of the instantaneous output beam power of the laser 2. But, after a period of time, due to the capacitive nature of the pyroelectric detector, charge builds up on the capacitor, and there is no net charge to and from the pyroelectric detector 50. As a result, the instantaneous current output provided by the pyroelectric detector 50 during a train of pulses of the output beam has a DC bias, and is not a true indicator of the power of the output beam portion incident thereon.

Figure 3:
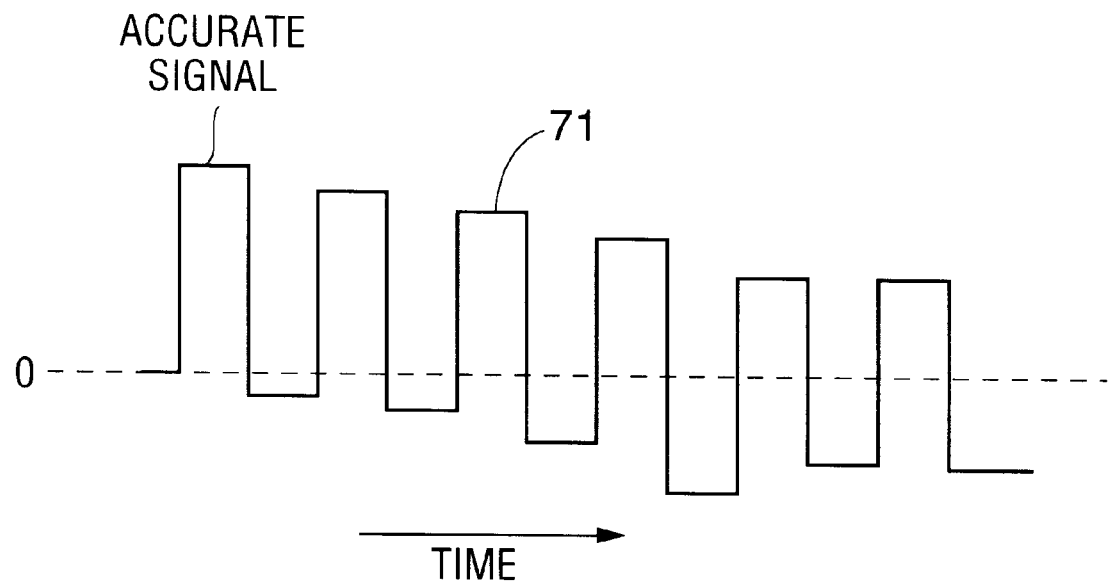
FIG. 3 shows the output of pyroelectric detector 50 of FIG. 2.
Figure 4:
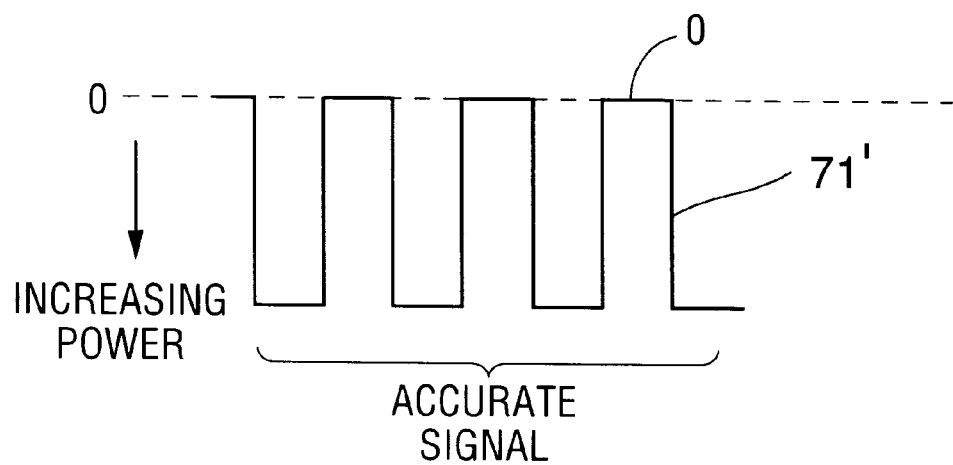
FIG. 4 shows the output of pyroelectric detector 50 of FIG. 2 after being DC restored by DC restorer 61.

This can be seen with reference to FIGS. 3 and 4. FIG. 3 is a graph of the power of an output beam portion from the laser 2. FIG. 4 is a graph of an example output of a ceramic insulator pyroelectric detector 50, over time, upon which the output beam portion whose power is shown in FIG. 3A is incident. It can be seen from FIGS. 3 and 4 that, after a number of pulses of output beam 3, the current output (i.e., charging of the capacitor) of pyroelectric detector 50 during a pulse is biased by an amount equal to the current output (i.e., discharging of the capacitor) during the previous pulse off time.

Referring again to FIG. 2, to obtain an accurate indication of the cumulative energy in each pulse of output beam 3 from pyroelectric detector 50, the amplified output of the pyroelectric detector 50 (i.e., the output of transimpedance amplifier 12A) is provided to a DC restorer 61 when the laser 2 is off, and the DC restorer 61 is configured to hold this amplified voltage. Then, when the laser 2 is turned on (as indicated to the DC restorer 61 by the RESET2 signal being deasserted), DC restorer 61 is configured to provide the held voltage as a correction voltage signal at the output of the DC restorer 61. Then, while the laser 2 is on, the DC restorer provides the correction voltage signal to the integrator 12B, thus biasing the amplified voltage value provided from the transimpedance amplifier 12A when the laser is on.

The value "O" can be prestored in memory unit 66A (which is addressable by microprocessor 66) and microprocessor 66 can be programmed to compute the quantity T=E−O (and assert the corresponding digital data value to D-to-A converter 70) in response to each user-selected beam pulse energy value E. Preferably, the estimated value of "O" is continuously updated based on the current performance of the laser 2. In particular, the laser outputs a sequence of output beam pulses (all intended to have the same user-selected beam pulse energy E). For each output beam pulse, timer 63 does not disable integrator 12B until after termination of the output beam pulse (e.g., by waiting approximately 200 μs after assertion of the clear signal by comparator 72). Thus, the "final" output signal from peak hold circuit 60 (i.e., the signal output from circuit 60 after termination of the output beam pulse) is indicative of the total output beam pulse energy from beginning through termination of the pulse. The final output signal from circuit 60 is digitized in A-to-D conversion circuit 62, and the digitized final output signal is fed back to processor 66. Once processor 66 has obtained the digitized final output signal, timer 63 resets peak/hold circuit 60. Processor 66 computes the difference between the digitized final output signal, which represents measured total energy of the most recent ("nth") output beam pulse, and the user-selected value E. Processor 66 then uses the difference as a feedback signal to generate an improved estimate ($O_{n+1}$) of the offset value (O) for terminating the next output beam pulse (the "n+1 th" output beam pulse), and then asserts an improved threshold digital data value, $T_{n+1}=E-O_{n+1}$, to digital-to-analog converter 70. Comparator 72 compares the resulting analog threshold signal output from circuit 70, to the output of integrator 12B, during the next output beam pulse. In other words, processor 66 is programmed with software for generating a first threshold value $T_1=E-O_1$ during production of a first one of the output beam pulses, where $O_1$ is an estimate of the offset value O, and for generating a second threshold value $T_2=E-O_2$ during production of the next one of the output beam pulses, where $O_2$ is an improved estimate of the value O.

In other embodiments, a look-up table containing a set of N values $T_i=(E_i-O_i)$ is prestored in memory unit 66A, where N is an integer greater than one. The value of component $O_i$ of each look-up table entry $T_i$ need not be the same for all the look-up table entries. Thus, the look-up table values can consist of N values $T_i=E_i+O_i$, where $0<i<N+1$, where $E_i$ can have a different value for each index i, and $O_i$ can have a different value for each index i. In this class of embodiments, microprocessor 66 is programmed to read (in response to entry of each user-selected beam pulse energy value $E_i$) the stored look-up table value $T_i$ having the same index i, and to send the retrieved look-up table value to D-to-A converter 70.

With reference again to FIG. 2, analog-to-digital converter 76 may be provided to receive and digitize the analog output of D-to-A converter 70 and supplies the resulting digitized signal back to microprocessor 66 as a "read-back" signal, to check the operation of D-to-A converter 70. It should also be noted that the processor 66 can bypass the servo system by means of an "alignment enable" signal to switch 65. This causes switch 65 to provide alignment drive signals, from a fixed rate timer 67, to the laser power supply 16. This causes the laser 2 to produce pulses of a constant laser pulse width, thus facilitating manual alignment of the laser 2 and optical system by service personnel.

Figure 2:
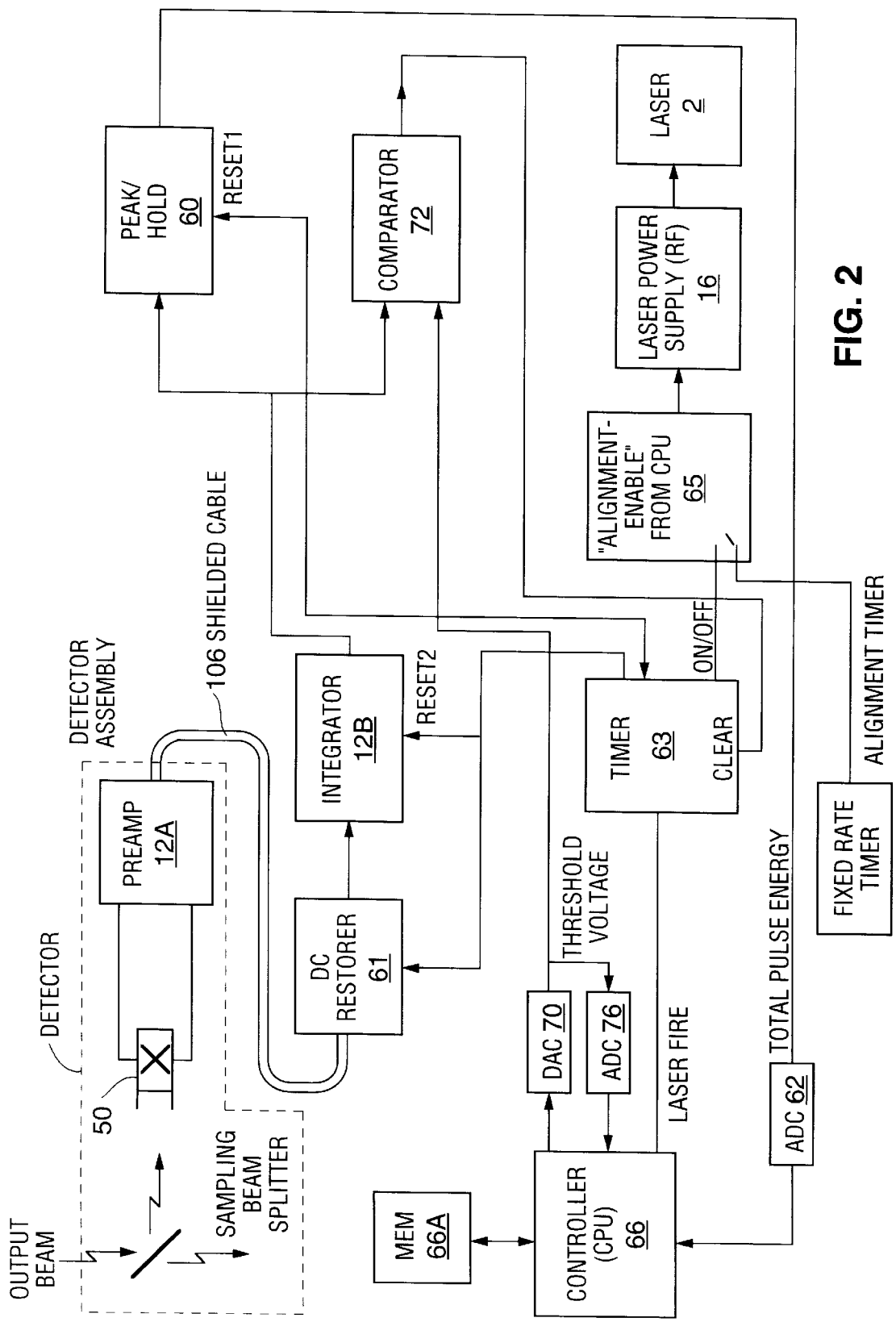
FIG. 2 is a block diagram of an embodiment of elements 10, 12, and 14 of FIG. 1.
Figure 5:
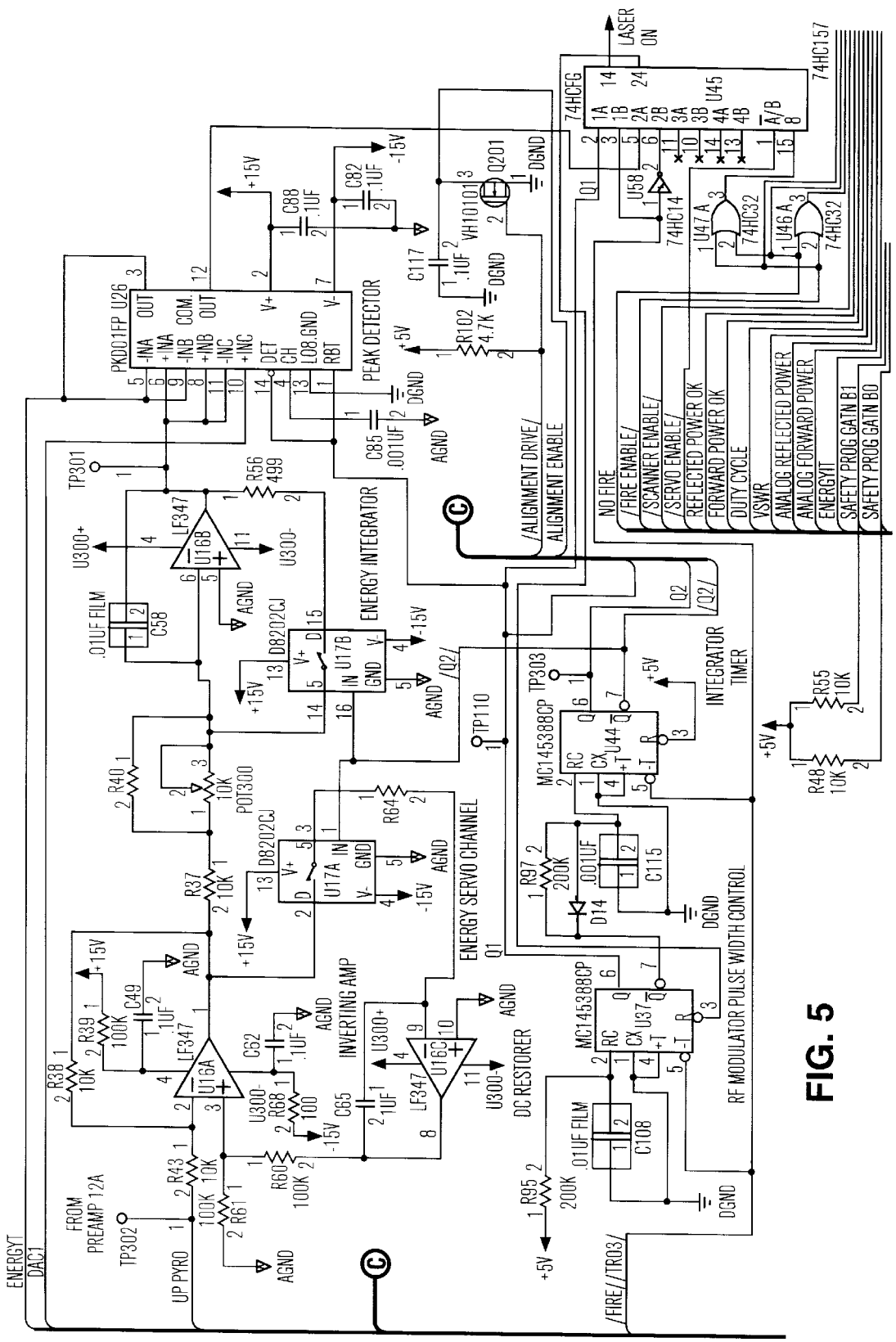
FIG. 5 schematically illustrates the embodiment of elements 10, 12, and 14 of FIG. 1.

Referring now to FIG. 5, a detailed schematic of the FIG. 2 circuit is provided. FIG. 6 (i.e., FIGS. 6A through 6G) provides a timing diagram of the significant signals generated in the FIG. 5 circuit. The amplified signal is provided from the pyroelectric detector and the amplifier 12A at TP 302. The amplified signal is shown in FIG. 6D. The amplified signal received at TP 302 is inverted at U16A (pins 1, 2, and 3). When the laser is off, switch U17A (pins 1 and 2) is on, which enables U16C of the DC restorer to drive U16A (pin 1) to zero volts.

During the period of laser output, U17A (pins 2 and 3) is open, so the voltage established at U16A (pin 3) is held. During the laser output pulse, U17B (pins 14 and 15) are open, so the integral of the DC-restored amplified signal is accumulated as charge and voltage in capacitor C58 (see FIG. 6E). Capacitor C58 is discharged during the laser pulse off time by U17B (pins 14 and 15).

The pulse energy signal appears at TP 301 and is applied to U26, which is a PKD-01 comparator and peak detector manufactured by Analog Devices. The laser energy is controlled by a threshold signal (see FIG. 6E) provided from the processor through DAC 1 to U26 (pin 10), the comparator "+" input. When the energy signal on U26 (pin 11), the comparator "−" input, exceeds the value of the threshold signal at the comparator "+" input, the laser power input is terminated by clearing timer U37, the "RF Modulator Pulse Width Control". (See FIGS. 6G and 6B). Timer U44 remains on such that the integration time is extended to measure the total pulse energy, including laser emission after the termination of the "laser on" command. (See FIGS. 6C. Also, FIG. 6E shows the "overshoot" laser emission.) As discussed above, the processor 66 may compare the total pulse energy with the desired energy to iteratively correct the threshold signals provided by the processor 66 on subsequent pulses. Thus, variations of laser efficiency and starting delay are corrected continuously during treatment.

Figure 7:
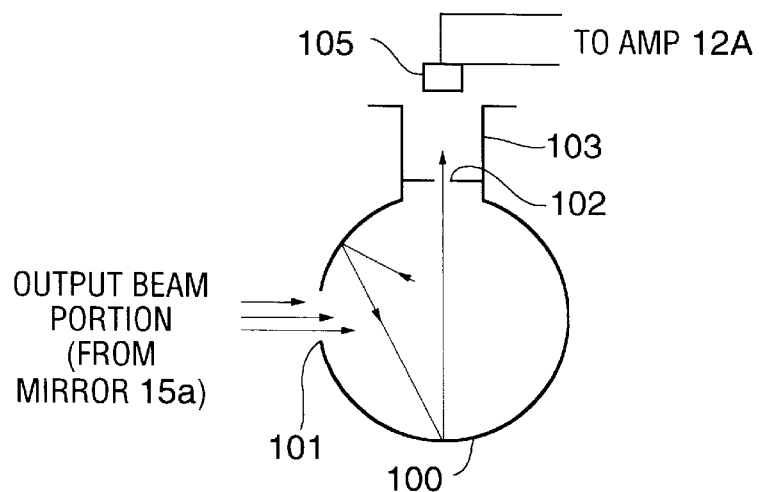
FIG. 7 illustrates a possible implementation of detector 10 of FIG. 1.

Several preferred implementations of detector 10 of FIG. 1 will next be described with reference to FIGS. 7, 8, and 9. In the FIG. 7 embodiment, reflective sphere 100 is positioned to receive a portion of output beam 3 that has been diverted by reflecting from partially reflective element 4 (shown in FIG. 1). This beam portion propagates through aperture 101 in sphere 100, and undergoes multiple reflections from sphere 100's diffuse reflecting inside surface. Most of the diffusely reflected beam energy eventually propagates through output aperture 102 into cylindrical element 103. The inner cylindrical surface of element 103 is highly absorptive of the beam radiation. The portion of the diffusely reflected beam that propagates through aperture 102 and is not absorbed by element 103 is incident with uniform radiation density on the surface of pyroelectric detector 105. The incident radiation density at detector 105 is desirably lower than at inlet aperture 101.

The output voltage signal from pyroelectric detector 105 is amplified by amplifier 12A and the amplified signal propagates over coaxial line 106 to DC restorer 61. The DC restored signal undergoes integration and, after integration, it is indicative of the cumulative energy in output beam 3.

Figure 8:
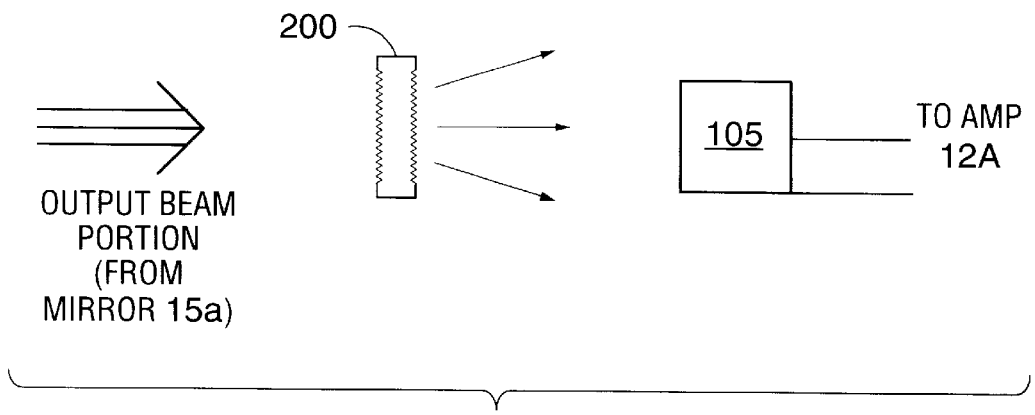
FIG. 8 illustrates a second possible embodiment of detector 10 of FIG. 1.

In the alternative embodiment shown in FIG. 8, a portion of output beam 3 that has been diverted by reflecting from partially reflective element 4 (shown in FIG. 1) is incident on transmissive diffusing plate 200. Much of the diffuse beam energy transmitted through plate 200 is incident with uniform radiation density on the surface of pyroelectric detector 105. The incident radiation density at detector 105 is desirably lower than that at plate 200.

Figure 9:
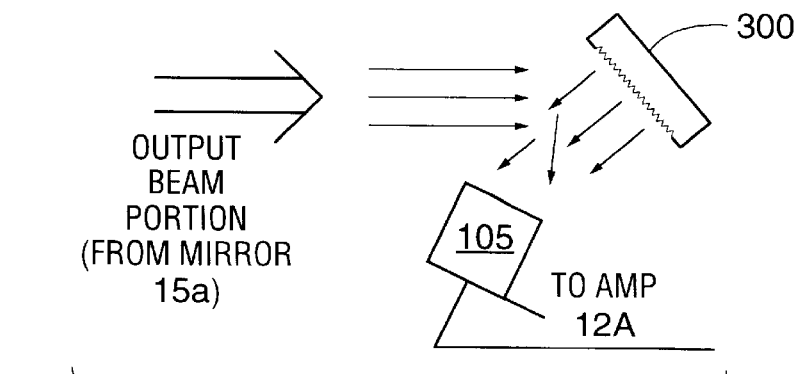
FIG. 9 illustrates a third possible embodiment of detector 10 of FIG. 1.

In the second alternative embodiment shown in FIG. 9, a portion of output beam 3 that has been diverted by reflecting from partially reflective element 4 (shown in FIG. 1) is incident on reflective diffusing plate 300. Much of the diffuse beam energy reflected from plate 300 is incident with uniform radiation density on the surface of pyroelectric detector 105. The incident radiation density at detector 105 is desirably lower than that at plate 300.

Figure 10:
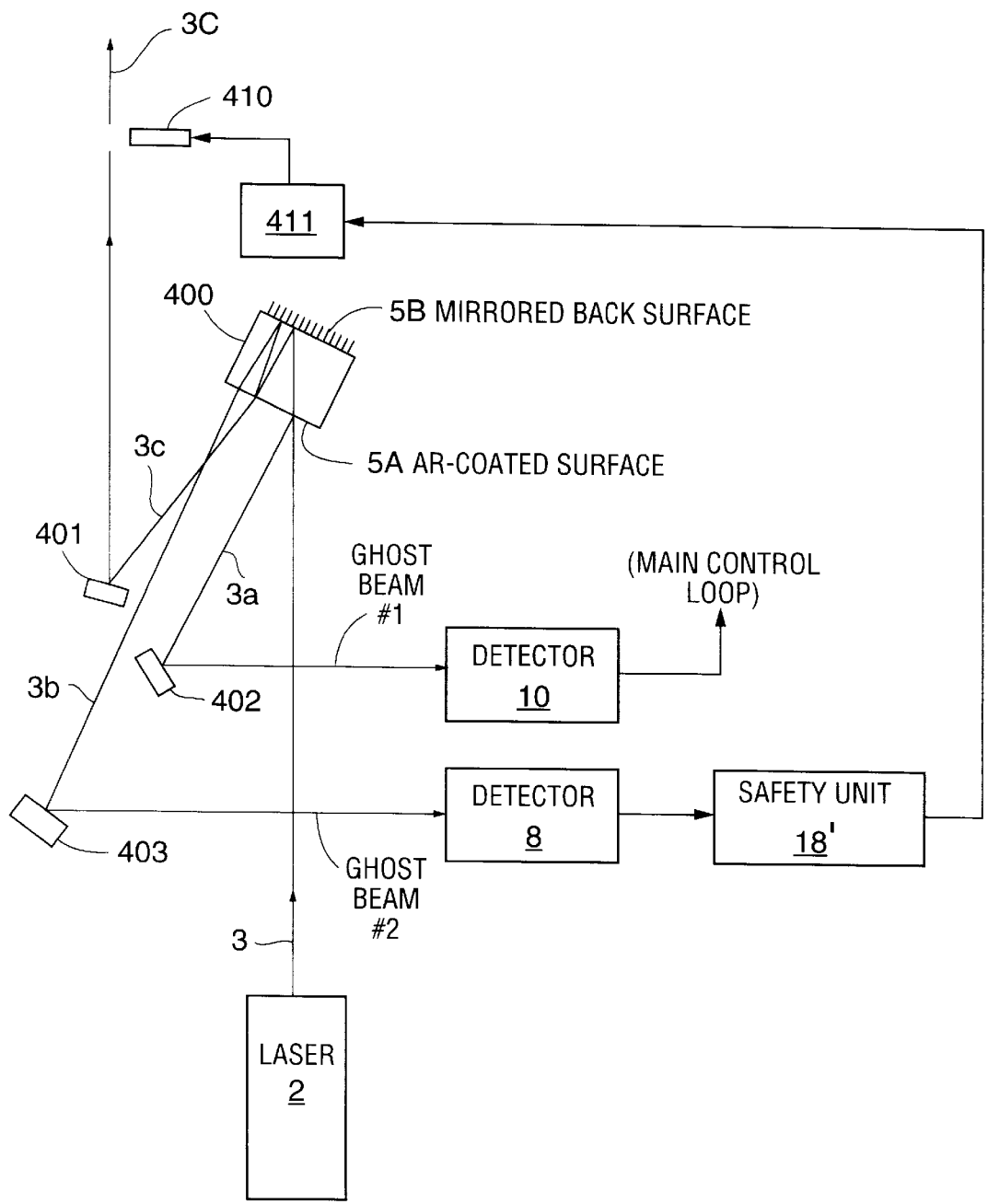
FIG. 10 is a block diagram of an alternative embodiment of the optical sampling subsystem of the FIG. 1 embodiment.

Next, with reference to FIG. 10, an alternative preferred embodiment of the optical sampling subsystem of the FIG.

1 embodiment will be described. In FIG. 10, output laser beam 3 emerges from laser 2 and is incident on beam splitting mirror 400. Mirror 400 has a front surface 5A having an anti-reflective coating, and a highly reflective back surface 5B. A small portion 3A of beam 3 reflects from front surface 5A and is incident on mirror 402, and a second small portion 3B of beam 3 reflects from front surface 5A and is incident on mirror 403. Most of the energy in beam 3 reflects from back surface 5B and is incident (as output beam 3C) on mirror 401.

Portion 3A of beam 3 reflects from mirror 402 and is then incident at detector 10 (whose output is supplied to integrating circuit 12 shown in FIG. 1). Portion 3B of beam 3 reflects from mirror 403 and is then incident at detector 8. The output of detector 8 is supplied to safety unit 18' (which can be identical to safety unit 18 shown in FIG. 1).

Mirror 401 reflects output beam 3C in a desired direction. Translatable safety shutter 410 is positioned along the path of output beam 3C. In its retracted position (shown in FIG. 6), shutter 410 does not block delivery of beam 3C. In response to a control signal (such as a shutter control signal from safety unit 18' indicative of an unsafe system operating condition), safety shutter actuator 411 moves safety shutter 410 (toward the left in FIG. 6) into an extended position across the path of beam 3C thereby blocking delivery of beam 3C. The provision of the safety loop (comprising elements 403, 8, 18', 411, and 410) ensures that failure of detector 10 (or any of the hardware or software for processing the output of detector 10) will not cause injury to a patient to whom output beam 3C may be directed.

Figure 11:
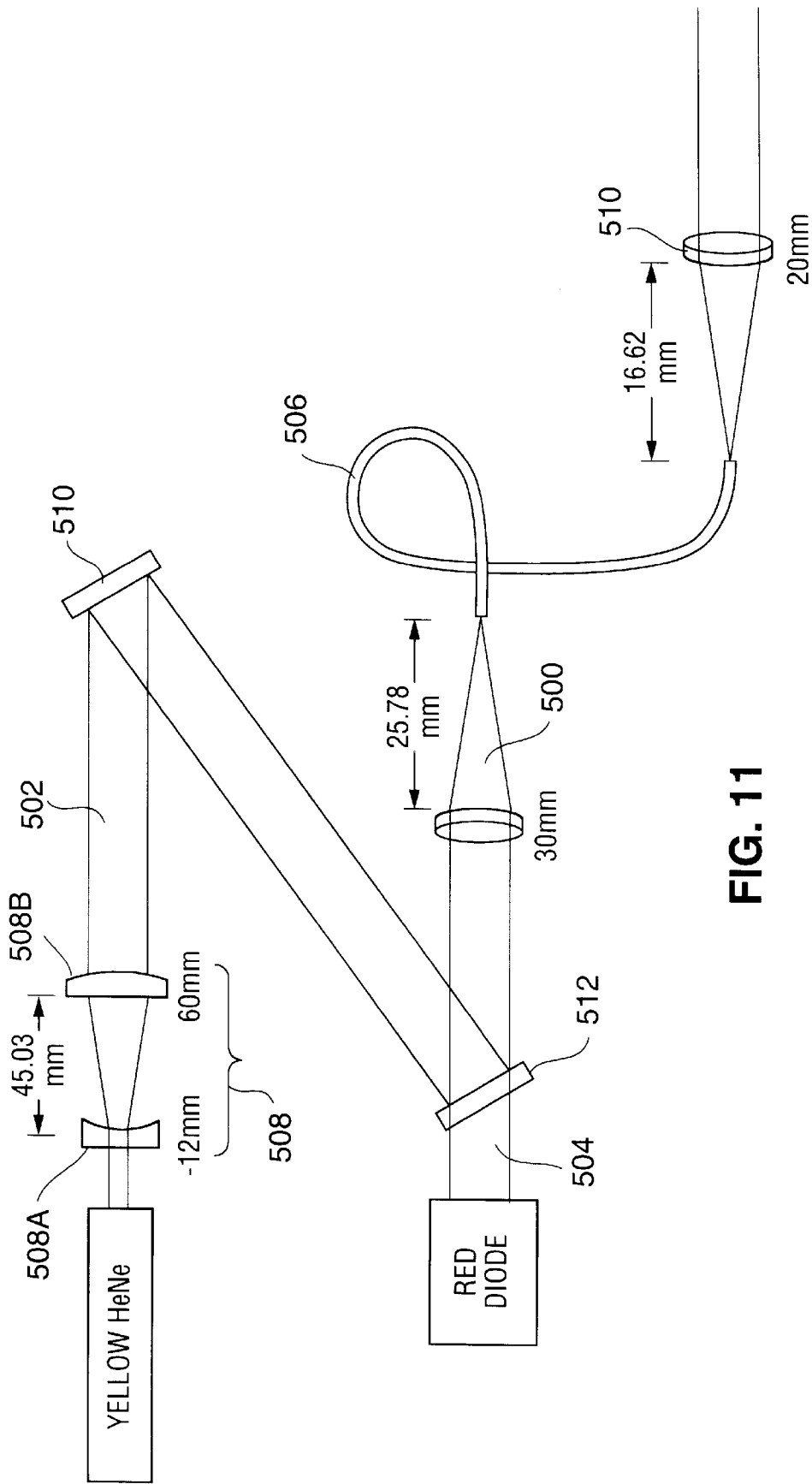
FIG. 11 is a block diagram of an aim beam system for use in aiming a treatment laser beam.

FIG. 11 is a block diagram of an aim beam system for use in aiming a treatment laser beam. In previous laser systems, it was difficult (if not impossible) to predict the diameter of a treatment beam, at its focal point on target tissue, using an aim beam. The FIG. 11 aim beam system solves this problem by matching the beam product of the aim beam with the beam product (i.e., the product of the waist size and the divergence angle) of the treatment beam. The aim beam is focused to match the diameter and divergence of the treatment beam. Then, however the beams (i.e., the aim beam and the treatment beam) are processed, they will always have the same diameter. The aim beam 500 produced by the FIG. 11 system includes both a yellow aim beam 502 and a red aim beam 504, which allows for optimal aiming of a treatment beam onto different color tissue. Both the yellow aim beam 502 and the red aim beam 504 are conditioned to have a beam product which is roughly equal to the treatment beam (which may be, e.g., produced by a $CO_2$ laser).

An optical fiber 506 is used to perform this conditioning. The proper beam product is achieved by choosing a fiber core diameter and selecting the input angle of the light and numerical aperture of the optical fiber 506 to produced the desired beam divergence angle exiting the optical fiber 506. In one embodiment, an optical fiber having a numerical aperture of 0.12 and a core diameter of 100 microns was employed. Then, a lens 510 is used to focus the beam diverging from the optical fiber 506 to match the beam size and divergence of the treatment beam. As a result, the aiming beam 500 and the treatment beam propagate with the same spatial characteristics.

Figure 12:
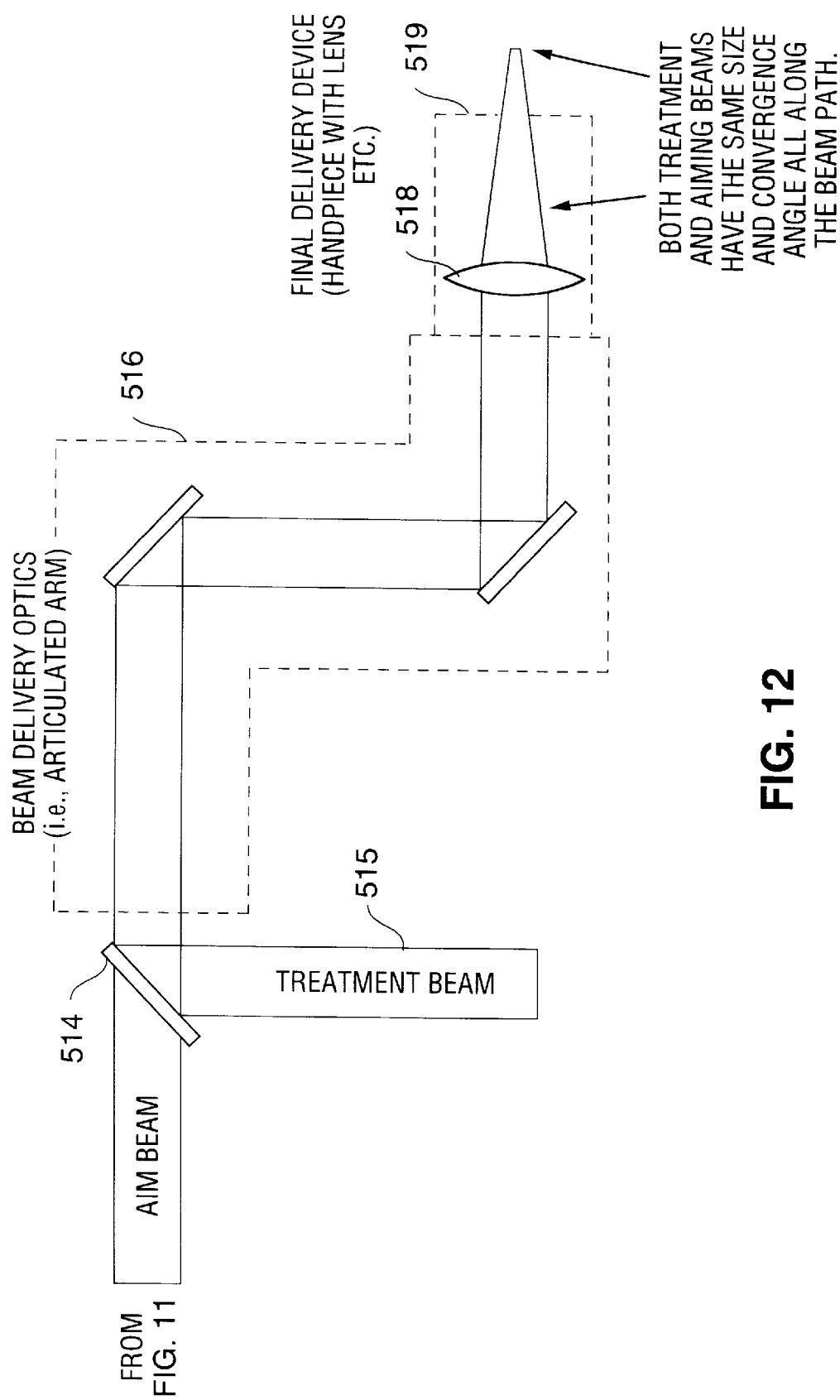
FIG. 12 is a block diagram of a patient delivery system that combines aiming and treatment beams.

Referring still to FIG. 11, a galilean telescope 508 (consisting of lenses 508A and 508B) enlarge the beam produced by a yellow HeNe laser to have a diameter equal to the major diameter of the elliptical beam produced by a red diode laser. The enlarged yellow aim beam 502 and the elliptical red aim beam 504 are combined in a dichroic combiner 512 and focused into the end of an optical fiber 506. Finally, the aim beam output from the optical fiber 506 is focused by lens 510. Referring now to FIG. 12, the focussed aim beam is combined by a combiner 514, with a treatment beam 515, and propagated to the end of an articulated arm 516 (see FIG. 12) at approximately the same diameter as 515. The combined beams are focussed by a lens 518 in a handpiece 519. The beam output from the handpiece 519 includes the aim beam and the treatment beam at (the end of the articulated arm) approximately the same diameter.

Various modifications and alterations in the structure and method of operation of this invention will be apparent to those skilled in the art without departing from the scope and spirit of this invention. Although the invention has been described in connection with specific preferred embodiments, it should be understood that the invention should not be unduly limited to such specific embodiments.

What is claimed is:

1. A pulsed laser system, including:
    a laser;
    a power supply for supplying a train of input power pulses to the laser, wherein the laser produces a train of output beam pulses in response to the train of input power pulses;
    a user interface permitting the user to select a desired energy per output beam pulse;
    beam energy measurement means for generating a beam energy signal indicative of cumulative energy of one of said output beam pulses; and
    control means for generating a termination control signal in response to determination that the cumulative energy of said one output beam pulse matches a threshold value, sending the termination control signal to the power supply to cause the power supply to terminate the input power pulse in response to said termination control signal, and generating the threshold value to have a particular value, T, representing a threshold output beam pulse energy lower than the user selected energy, E, of the output beam pulse, wherein the particular value T is determined based upon the selected energy E, thus compensating for inherent delay between generation of the control signal and termination of the output beam pulse in response thereto.

2. The system of claim 1, wherein the threshold value is a value T=E+O, where E is the user selected energy of the output beam pulse and O is an estimate of the output beam pulse energy accumulated during an inherent delay period in which the control signal is generated and determined based on the selected energy, and wherein the control signal is supplied to the power supply, and the output beam pulse is terminated in response to the control signal.

3. The system of claim 2, wherein the control means includes:
    a comparator, having inputs which receive the threshold value and the beam energy signal and an output asserting a match signal when the cumulative energy of the output beam pulse matches the threshold value; and
    a logic means for receiving the match signal and generating the termination control signal in response to the match signal, wherein the inherent delay period includes a control signal generation period in which the logic means generates the control signal.

4. The system of claim 2, wherein the power supply supplies a sequence of input power pulses to the laser, the laser produces a sequence of output beam pulses in response to the input power pulses, the beam energy measurement means generates a beam energy signal indicative of cumulative energy of each of the output beam pulses, the control means generates a control signal in response to determination that the cumulative energy of each of the output beam pulses matches one of a sequence of threshold values, and the control means generates each of the threshold values in a manner compensating for inherent delay between generation of one said control signal and termination of a corresponding one of the output beam pulses, wherein the control means includes:

a processor programmed with software for generating a first threshold value $T_1 = E - O_1$ during production of a first one of the output beam pulses, where $O_1$ is an initial estimate of said value O, and for generating a second threshold value $T_2 = E - O_2$ during production of a second one of the output beam pulses, where $O_2$ is an improved estimate of said value O.

5. The system of claim 2, wherein the control means includes:

a memory storing a look-up table of threshold values $T_i = E_i + O_i$, where "i" is an integer in a range $0 < i < N+1$, N is an integer greater than one, values $E_i$ are desired output beam pulse energy values, and values $O_i$ are delay compensation values; and a processor connected to the memory and capable of addressing the memory, wherein the processor is programmed to retrieve one of the threshold values $T_i$ from the memory in response to assertion of a corresponding one of the desired output beam pulse energy values $E_i$ to said processor.

6. The system of claim 5, also including:

an input device connected to the processor, for asserting said corresponding one of the desired output beam pulse energy values $E_i$ to the processor.

7. The system of claim 1, wherein the output beam pulse propagates along a beam path, and the beam energy measurement means includes:

a pyroelectric detector;

a beam sampling means positioned along the beam path for diverting a portion of the output beam pulse to the pyroelectric detector; and an integration means for receiving from the detector a power signal indicative of power of said portion of the output beam pulse, and integrating the power signal to generate the beam energy signal.

8. The system of claim 7, wherein the beam sampling means includes:

a diffractive optic that diverts the portion of the beam pulse by diffraction; and an imaging mirror that reflects the diverted portion of the beam to the pyroelectric detector.

9. The system of claim 7, wherein the pyroelectric detector includes a reflective sphere having a generally spherical wall with an input aperture and an output aperture through said wall, with the input aperture aligned for receiving the portion of output beam, and a reflecting inner spherical surface for diffusely reflecting said portion of output beam through the output aperture.

10. The system of claim 7, wherein the beam sampling means is a transmissive diffusing plate.

11. The system of claim 7, wherein the beam sampling means is a reflective diffusing plate.

12. The system of claim 7, also including:

a second beam sampling means positioned along the beam path for diverting a second portion of the output beam pulse from the beam path; and safety means for receiving and processing the second portion of the output beam pulse and generating a second control signal for terminating delivery of the output beam pulse when said processing of the second portion of the output beam pulse indicates an unsafe operating condition.

13. The system of claim 12, wherein the second beam sampling means includes:

a second diffractive optic that diverts the second portion of the beam by diffraction; and a second imaging mirror that reflects the second, diffracted, portion of the beam to the safety means.

14. The system of claim 12, also including:

a movable shutter capable of moving into a position blocking the beam path in response to the second control signal, wherein the safety means is connected to the shutter to supply said second control signal to the shutter.

15. The system of claim 7, wherein the control means is further for generating a sequence of commencement signals to the power supply, for causing the power supply to generate a sequence of input power pulses such that the laser produces a sequence of output beam pulses, and the system further comprising:

correction circuitry that samples the power signal from the detector between a current output beam pulse and an output beam pulse immediately previous to said current output beam pulse and that holds the sampled power signal; and combiner circuitry that, during said current output beam pulse, combines the held, sampled power signal with the power signal from the detector to produce a corrected power signal wherein the integrator means receives the corrected power signal from the combiner circuitry and integrates the corrected power signal to generate the beam energy signal.

16. The system of claim 15, and further including selection circuitry that couples the correction circuitry to receive the power signal from the detector in response to a commencement signal being generated by said control means and that decouples the correction circuitry to receive the power signal from the detector in response to a termination signal being generated by said control means.

17. The system of claim 16, wherein the correction circuitry includes circuitry that tracks a level of the power signal while the selection circuitry couples the correction circuitry to receive the power signal, and that otherwise holds the level of the received power signal at a time when the selection circuitry decouples the correction circuitry to receive the power signal.

* * * * *